US010239236B2

(12) United States Patent
Chowdhury

(10) Patent No.: US 10,239,236 B2
(45) Date of Patent: Mar. 26, 2019

(54) MICRONEEDLE DEVICE AND METHOD OF PREPARATION

(71) Applicant: Dewan Fazlul Hoque Chowdhury, Loughborough (GB)

(72) Inventor: Dewan Fazlul Hoque Chowdhury, Loughborough (GB)

(73) Assignee: NDM Technologies Limited, Loughborough (GB)

(*) Notice: Subject to any disclaimer, the term of this patent is extended or adjusted under 35 U.S.C. 154(b) by 530 days.

(21) Appl. No.: 14/913,289

(22) PCT Filed: Aug. 18, 2014

(86) PCT No.: PCT/GB2014/052522
§ 371 (c)(1),
(2) Date: Feb. 19, 2016

(87) PCT Pub. No.: WO2015/025139
PCT Pub. Date: Feb. 26, 2015

(65) Prior Publication Data
US 2016/0207227 A1 Jul. 21, 2016

(30) Foreign Application Priority Data
Aug. 20, 2013 (GB) .................................. 1314902.6

(51) Int. Cl.
*A61M 37/00* (2006.01)
*B29C 31/00* (2006.01)

(52) U.S. Cl.
CPC ....... *B29C 31/008* (2013.01); *A61M 37/0015* (2013.01); *A61M 2037/0053* (2013.01)

(58) Field of Classification Search
None
See application file for complete search history.

(56) References Cited

U.S. PATENT DOCUMENTS 6,050,988 A * 4/2000 Zuck ................. A61B 5/14514
604/890.1
2008/0195035 A1 8/2008 Frederickson
(Continued)

FOREIGN PATENT DOCUMENTS

JP 2006/345984 12/2006
WO WO 2012/153266 11/2012

OTHER PUBLICATIONS

International Search Report and Written Opinion dated Dec. 12, 2014 for International Application No. PCT/GB2014/052522, Applicant, Dewan Fazlul Hoque Chowdhury (9 pages).

*Primary Examiner* — Barbara J Musser
(74) *Attorney, Agent, or Firm* — McCracken & Gillen LLC

(57) ABSTRACT

Microneedle devices have projections that are generally sharp and elongated and designed to disrupt the upper layer of the skin, cause micro-indentations, or pierce the skin. High density arrays are produced using micro-fabrication or micro-molding techniques. The assembly of individual needles does not lend itself to the production of high density arrays. A method of forming microneedle arrays is disclosed which comprises attaching a plurality of microneedles to a substrate, and building up a 2-dimensional microneedle array by wrapping layers of the substrate around a core or folding the layers repeatedly back upon themselves. The arrays are capable of needle densities with a pitch within the range of needle radius plus several micrometers to millimeters.

11 Claims, 2 Drawing Sheets

(56) References Cited

U.S. PATENT DOCUMENTS

Figure 1:
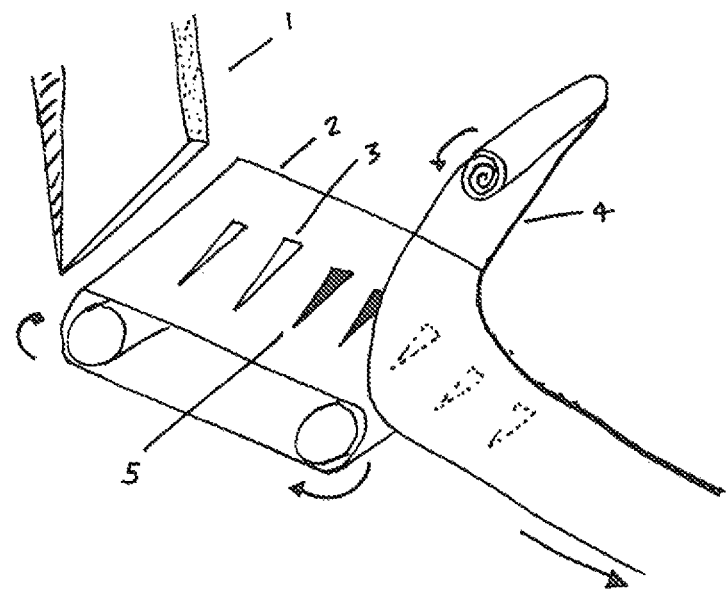

2010/0256568 A1 10/2010 Frederickson
2012/0263919 A1 10/2012 Ferguson

* cited by examiner

MICRONEEDLE DEVICE AND METHOD OF PREPARATION

FIELD OF THE INVENTION

The present invention relates to microneedle arrays, and in particular to a method of forming a microneedle array.

BACKGROUND TO THE INVENTION

Microneedles have been in use in cosmetic treatments for collagen induction therapy for over a decade. More recently microneedles have been developed for drug delivery applications. The methods of applying the drug using microneedles include needles produced from drug that is inserted into the skin, solid needles coated with drug that dissolves in the skin, hollow needles with a bore via which drug is forced into the skin, creation of pores in the skin followed by application of drug on top of the skin/pores, and creation of pores followed by placement of drug directly above or into the skin.

Needles produced using fabrication techniques lend themselves to high needle densities. However it is often preferable to produce needles from stainless steel metal and other solids, from the point of view of tip sharpness and mechanical strength. These needles when assembled are generally of low density, as the density is restricted as a result of the proximity of needles and methods available to place them and secure them at such close proximities. It would be desirable therefore to attain a commercially viable process to produce high density needle arrays using individual solid or hollow needles.

SUMMARY OF THE INVENTION

This invention provides a method for forming a microneedle array, the method comprising the steps of:
  attaching a plurality of microneedles to a substrate, the microneedles being arranged generally flat against the substrate; and
  building up a 2-dimensional array from layers of the substrate.

The microneedles may be produced from plastic, metal, ceramic, or drug, or any other material known in the current state of the art. These may be solid or hollow. They will be generally elongated structures with a sharp or blunt tip, with a diameter in the range of 1 (at the tip) to 100's microns (main body), and they may be symmetrical or asymmetrical. In accordance with the invention, the needles are arranged along the substrate in a one-dimensional row, then layers of the substrate are built up to assemble a two-dimensional array of needles (the length of the needles extends along the third dimension). These arrays may be assembled from the rows in a rectangle, square, circular format or other format in-between, as required by the application. The needle arrays may be of uniform height or may be different heights within a given set of arrays to conform to the surface where it is intended to be applied. The needle arrays may be compressible or completely rigid when depressed in the downward direction, i.e. parallel to the length of the needles. Some needles may be compressible whilst others may be rigid within the same array(s). The word needle is used to describe micron to millimeter sized projections that are generally longitudinal in shape, and application is intended to imply any surface upon which the needles may be applied, which may be human, non-human animal, or an inanimate object surface, for example for the purposes of diagnostics, the application of the needle array to a biological sample.

According to the present invention it is possible to produce arrays with a needle pitch that is the size of the needle diameter plus several to 10's of micrometers. The process for producing the arrays can be a continuous process or batch process which does not require sophisticated equipment, and may be achieved using conventional manufacturing methods. The needles are individually aligned into slots or grooves in the correct orientation, sharp tip pointing in the direction of the outer face of the final array. Preferably the microneedles are arranged in parallel on a surface prior to being transferred to a substrate, in a plurality of needle receiving grooves. However in light of the size of the needles, it may be preferable to produce the needles with both ends sharp such that the needles will not require re-orientating. This will have the benefit of reducing the complexity of the assembly process. The needles can be aligned into slots that are of sufficient diameter to hold the needles in a longitudinal orientation, or the desired orientation, which may be at a slight angle to aid with application to the desired substrate. The alignment of the tips of the needles is achieved by having a flat surface against which the needle tips rest, either by gravity or by application of external force such as vacuum. Microneedles are preferably aligned on the surface under the influence of gravity, by inclining the surface laterally such that the needle tips come to rest against an adjacent wall. The needle height therefore is not required to be with fine tolerances, since the protruding portion of the needle, the tip, is aligned according to the desired height, and the upper portion is encased within a housing at a later step or may be sealed with a suitable material.

Once the needles are aligned they may be adhered by surface contact to an adhesive substrate, which may be double sided. Once the needles have been adhered in a continuous row or in small segments onto the adhesive tape, the tape may be wound round a core or onto itself to form straight arrays or to form concentric circles or a spiral that rolls onto itself until the desired diameter of device is achieved. Preferably, the step of building up layers involves wrapping the substrate around a core or folding it repeatedly back upon itself. The pitch between needles can be adjusted by adjusting the thickness of the substrate/tape and/or adhesive material. The pitch between adjacent microneedles is preferably equal to or greater than the width of a single microneedle.

The tape may be any standard medical grade polymer such as nylon, fabric, silicone, cellulose, polyester, etc., and the adhesive may be a pressure sensitive adhesive that may be medical grade, or it may be some other readily available industrial adhesive. The distance between the needles may be adjusted such that in the wound position, the distance between needles is controlled, and such that the density of the needles is controlled to provide the requisite pitch. The needle aligner and holder may contain channels for the needles that are equidistant throughout, or that are variable in distance as required to give the desired pattern on the needle array(s).

The invention also provides apparatus for forming a microneedle array, the apparatus comprising: a source of microneedles; a surface having a first position for receiving microneedles from the source; and a movable substrate adjacent a second position of the surface; wherein the surface is movable from the first to the second position.

Specifically, the surface is laterally inclined between the first and second positions in order to align a plurality of microneedles into a respective plurality a plurality of needle receiving grooves. In this regard, the grooves are aligned substantially perpendicular to the direction of movement of the surface so that the microneedles can be aligned under the influence of gravity. Most preferably, the surface is a conveyor for moving the microneedles from the first position to the second position.

Preferably the microneedles are sharp at both ends to avoid the need for re-orienting needles that are received on the surface, and a tip of each microneedle extends beyond an edge of the substrate.

Preferably the substrate is a tape or film so that layers of the substrate can easily be built up into an array, and further the substrate comprises a coating of adhesive so that microneedles are held securely in position along the substrate.

The needle arrays may subsequently be loaded into an applicator device, or interfaced to a drug reservoir to channel the drug along the side of the needles or through the bore of the needles. During loading into an applicator device the portion of the needles that are enclosed within the housing of the device may be further constrained by addition of adhesive, or resin, that may solidify upon drying or curing, to prevent the needles from falling out. Preferably the tips of the microneedles are secured together in a bed of resin. The length of the needle may be in the range of hundreds of microns to several millimeters.

DRAWINGS

Figure 2:
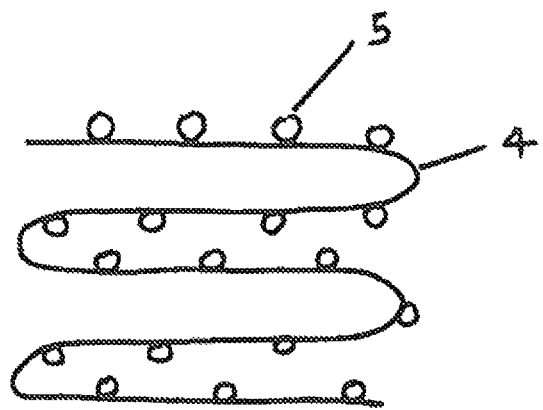
Figure 3:
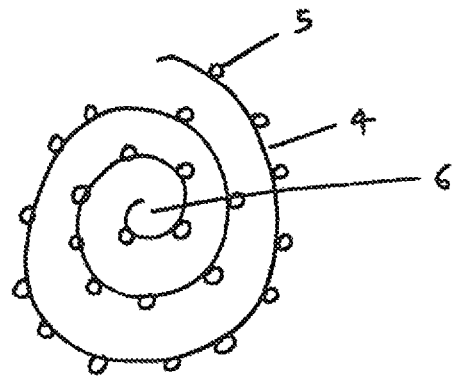
Figure 4:
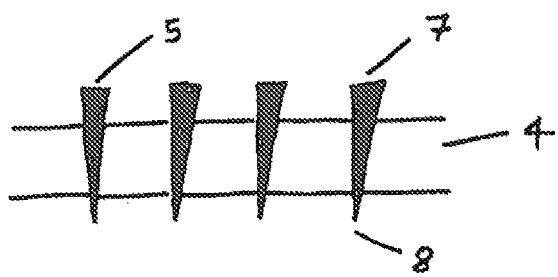
Figure 5:
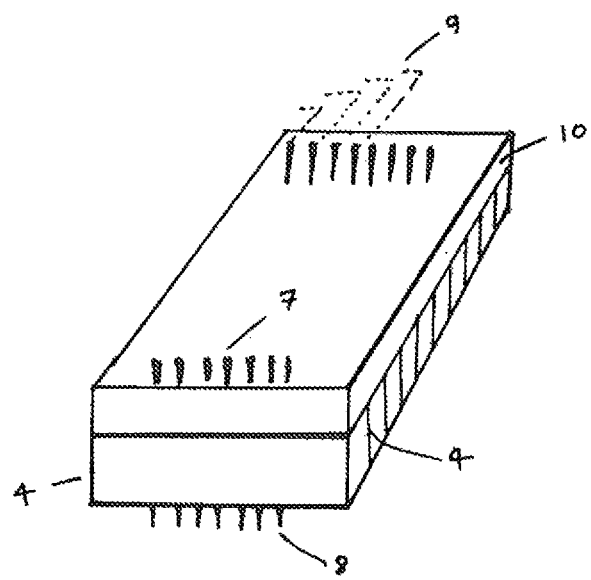

Specific embodiments of the invention are now described by way of example and with reference to the accompanying drawings in which like numerals are used to indicate like parts and where:

FIG. 1 shows an apparatus for forming a microneedle array according to an embodiment of the invention, FIG. 2 shows a cross-section of a microneedle array formed by folding layers of the substrate repeatedly back upon itself, FIG. 3 shows a cross-section of a microneedle array formed by wrapping the substrate around a core, FIG. 4 is a plan view of microneedles arranged on a substrate, and FIG. 5 shows a microneedle array with the microneedles secured in a bed of resin.

Referring now to the drawings, FIG. 1 shows a hopper 1 as a source of microneedles designed to feed the needles 5 in a specific orientation, on to a belt 2 with grooves 3. A separate adhesive roll, or substrate 4, makes surface-contact, or near surface-contact, and as a result adheres the needles 5 to the adhesive substrate 4 (as shown by the dotted lines to denote needles 5 adhered to the underside of the adhesive substrate 4). The hopper 1 has an opening that supplies needles 5 which are uniform and/or tapered at both ends. The belt 2 has a plurality of grooves 3 or slots into which the needles 5 are placed. The belt 2 is formed from metal, plastic or rubber. The needles 5 are not required to fit tightly in the grooves 3. While the belt 2 is shown in a horizontal configuration, it may also be inclined laterally at an appropriate angle to allow the tips of the needles 5 to rest against an adjacent wall (not shown) under the influence of gravity. This allows a uniform height of needle 5 to be achieved at the outer surface of the arrays, i.e. the face from which the needles 5 protrude from the final device. The substrate 4 is formed from foam or any standard tape material. If desired the substrate 4 need not be adhesive and may instead contain grooves or slots into which the needles 5 are directly placed, positioned and mechanically restrained before being wound together to form the desired needle array. A mechanical restraint could be a click lock slot that allows needles 5 to be clicked into position.

FIG. 2 shows a view in cross-section of an embodiment of the invention in which the needles 5 on the tape 4 can be shaped to produce an array, in a rectangular shape. The adhesive (not shown) may be single sided or it may be double sided. The thickness of the adhesive is used to ensure any gaps between the needle 5 and the adhesive is filled by adhesive flow. In its simplest form the needle array may be a single needle 5, or a single row of needles 5, arranged on a substrate 4 which conforms to a particular device housing, e.g., straight, circular, etc. Any gaps between the adhesive and the substrate 4 and the needles 5 are also filled using an insert to cover the edges of the substrate 4, or using silicone or another material that can be applied in liquid form which then solidifies, thus sealing out of sight the needle 5/substrate 4 edges that would otherwise be visible from the bottom face of the array. In the case of tapered needles 5, the tapered portion is generally very close to the tip. However where the tapered portion is along part of the length or the entire length of the needle 5 the upper portion, or the straight portion of the needles, are compressed or held together using an additional material such as a resin. Alternatively, they can be held by mechanical compression, for example, by applying tension on the adhesive substrate upper end to keep the needles 5 straight and prevent them from tapering inwards within the array.

FIG. 3 shows a view in cross-section of an alternative embodiment of the invention in which the needle 5 loaded substrate 4 is wound around a core 6 or around itself in a spiral configuration to form an array. The needle 5 loaded substrate 4 is wound around the core 6 until a desired diameter of device is achieved.

FIG. 4 is a schematic of the needles 5 adhered or connected to the substrate 4 leaving the upper 7 and lower 8 portions of the needles 5 exposed. In doing this the upper ends 7 of the needles 5 can be enclosed into a housing of the device and may further be secured using chemical or mechanical restraint means. For example, using resin or an adhesive mass that sets into a solid, preventing movement of the needles 5 in the lateral direction, and preventing the needles 5 from slipping out of the array where the needles 5 may be pierced into a hard material that offers resistance when pulling the needle array away from the surface. A significant benefit of using an adhesive based substrate 4 is that very large forces will be required to dislodge the needles 5 from the device due to the high surface area of contact between needle surface 5 and adhesive. Furthermore shear forces required to slide the needle 5 away from the adhesive are significantly higher than those required to peel the needle 5 from the adhesive, and by wrapping the needles 5 on themselves tension may be applied to provide additional compression on the adhesive and needle wall surfaces. Allowing the lower portion 8 of the needles 5 to be exposed further than their desired finished length will allow for a 'spacer' to be attached to adjust the height of the protruding portion of the needles 5 as required—or indeed for mechanically adjusting the height of the needles 5 protruding from the lower face using a mechanical screw for example to adjust the height.

FIG. 5 shows the substrate 4 wound or folded into a rectangle, with the lower portions 8 of the needles protruding from the base of the array, and the upper portions 7 of the needles protruding from the top of the array. The upper portions 7 are partially encased within a resin 10 or some other material to stabilize the needle array. The dotted lines 9 represent an optional electrical contact means to each individual needle via the upper portions 7 of the needles 5.

Microneedles 5 currently available on the market in either stamp like devices, such as dermapads available from Dermaroller®, or other roller devices have a pitch in the region of 1.5 mm from needle tip to tip for needles 5 with a diameter of 250-450 um. Assuming a 450 um diameter, this implies the distance between needle 5 walls is approximately 1 mm, or 1.25 mm in the case of 250 um diameter needles 5. This invention allows the needle 5 to be located on to a substrate 4 as thin as a few microns, thus achieving a pitch that is comparable to or smaller than that achieved using injection molding and micro-fabrication techniques, providing a significantly higher density of needles 5 which has very important applications for both drug delivery and diagnostic applications; the pitch may be as low as the diameter of the needle 5 plus the thickness of the adhesive/substrate 4. At one extreme where the substrate 4 is folded in on itself and the needles 5 are touching, the pitch is reduced to the diameter of the needles 5 at their widest point, i.e., the needles 5 would be touching thus the radius of each needle 5 at the widest region separates the needles 5, hence the pitch is equal to the needle 5 diameter at the widest point, or less in the case where the needles 5 are pointed towards each other.

In the case of diagnostic applications, a suitably designed printed circuit board could be mounted at the base of the upper part of the needle arrays (seated within the housing of a device for example) providing electrical contact and feedback/communication to and from individual needles 5 if desired. This is very difficult or impossible to achieve where needles 5 are micro-metal molded for example as the base of the needle 5 is the same substrate as the needles 5 themselves thus electrically connected as a single unit, rather than individual needle arrays.

The invention claimed is:

1. A method for forming a microneedle array, the method comprising the steps of: attaching a plurality of microneedles to a substrate, the microneedles being arranged generally flat against the substrate; and
building up a 2-dimensional array from layers of the substrate to which the microneedles are attached.

2. The method of claim 1, wherein the step of building up layers involves wrapping the substrate around a core or folding the substrate repeatedly back upon itself.

3. The method of claim 1, wherein the microneedles are arranged in parallel on a surface prior to being transferred to the substrate.

4. The method of claim 3, wherein the surface has a plurality of needle receiving grooves.

5. The method of claim 4, further comprising aligning the microneedles on the surface under the influence of gravity.

6. The method of claim 1, wherein the pitch between adjacent microneedles is equal to or greater than the width of a single microneedle plus 100 micrometers.

7. The method of claim 1, wherein the substrate is a tape or a film.

8. The method of claim 1, wherein the substrate comprises a coating of adhesive.

9. The method of claim 1, wherein a tip of each microneedle extends beyond an edge of the substrate.

10. The method of claim 9, further comprising securing the microneedle tips together in a bed of resin.

11. A microneedle array formed according to the method of claim 1.

* * * * *